United States Patent
Cheng

(10) Patent No.: US 9,068,918 B2
(45) Date of Patent: Jun. 30, 2015

(54) ELECTRON RADIATION MONITORING SYSTEM TO PREVENT GOLD SPITTING AND RESIST CROSS-LINKING DURING EVAPORATION

(71) Applicant: SKYWORKS SOLUTIONS, INC., Woburn, MA (US)

(72) Inventor: Kezia Cheng, Lowell, MA (US)

(73) Assignee: SKYWORKS SOLUTIONS, INC., Woburn, MA (US)

( * ) Notice: Subject to any disclaimer, the term of this patent is extended or adjusted under 35 U.S.C. 154(b) by 407 days.

(21) Appl. No.: 13/678,765

(22) Filed: Nov. 16, 2012

(65) Prior Publication Data

US 2013/0069622 A1  Mar. 21, 2013

Related U.S. Application Data

(63) Continuation of application No. 12/831,855, filed on Jul. 7, 2010, now Pat. No. 8,373,427.

(60) Provisional application No. 61/303,040, filed on Feb. 10, 2010.

(51) Int. Cl.
*G01R 27/08* (2006.01)
*G01N 27/00* (2006.01)
(Continued)

(52) U.S. Cl.
CPC .................. *G01N 27/00* (2013.01); *Y10T 29/41* (2015.01); *H01J 37/304* (2013.01); *H01J 37/3053* (2013.01); *H01J 2237/30472* (2013.01); *H01J 2237/3132* (2013.01); *H01L 21/02* (2013.01)

(58) Field of Classification Search
CPC .................................. G01N 27/00; G01R 27/08
USPC ........................................... 324/694; 29/25.01
See application file for complete search history.

(56) References Cited

U.S. PATENT DOCUMENTS 3,087,838 A    4/1963  Lubin
4,987,857 A    1/1991  Aketagawa et al.
(Continued)

FOREIGN PATENT DOCUMENTS

JP    58122930 A    7/1983
JP    01208448 A    8/1989
(Continued)

OTHER PUBLICATIONS

Notification of Transmittal of the International Search Report and the Written Opinion of the International Searching Authority dated Nov. 1, 2011 for International Application No. PCT/US2011/022260.
(Continued)

*Primary Examiner* — Benjamin M Baldridge
(74) *Attorney, Agent, or Firm* — Lando & Anastasi, LLP

(57) ABSTRACT

Disclosed herein are systems and methods for in-situ measurement of impurities on metal slugs utilized in electron-beam metal evaporation/deposition systems, and for increasing the production yield of a semiconductor manufacturing processes utilizing electron-beam metal evaporation/deposition systems. A voltage and/or a current level on an electrode disposed in a deposition chamber of an electron-beam metal evaporation/deposition system is monitored and used to measure contamination of the metal slug. Should the voltage or current reach a certain level, the deposition is completed and the system is inspected for contamination.

20 Claims, 12 Drawing Sheets

(51) Int. Cl.
 *H01J 37/304* (2006.01)
 *H01J 37/305* (2006.01)
 *H01L 21/02* (2006.01)

(56) References Cited

U.S. PATENT DOCUMENTS

| | | | |
|---|---|---|---|
| 5,851,842 | A | 12/1998 | Katsumata et al. |
| 7,148,705 | B2 | 12/2006 | Maeno |
| 7,709,062 | B2 | 5/2010 | Shichi et al. |
| 7,754,503 | B2 | 7/2010 | Sasaki et al. |
| 8,373,427 | B2 | 2/2013 | Cheng |
| 2002/0145396 | A1 | 10/2002 | Gordon et al. |
| 2003/0066975 | A1* | 4/2003 | Okada .................. 250/492.2 |
| 2004/0100290 | A1 | 5/2004 | Pope et al. |
| 2005/0045822 | A1* | 3/2005 | Onishi ...................... 250/311 |
| 2007/0045534 | A1* | 3/2007 | Zani et al. ............... 250/309 |
| 2007/0155185 | A1 | 7/2007 | Rauf |
| 2008/0018460 | A1* | 1/2008 | Ishiguro et al. .......... 340/540 |
| 2008/0223409 | A1* | 9/2008 | Horsky et al. ........... 134/22.1 |
| 2010/0221612 | A1* | 9/2010 | Richard .................. 429/231.6 |
| 2011/0027408 | A1 | 2/2011 | Suzuki et al. |

FOREIGN PATENT DOCUMENTS

| | | |
|---|---|---|
| JP | 03226559 A | 10/1991 |
| JP | 03291370 A | 12/1991 |
| TW | 201002841 A | 1/2010 |

OTHER PUBLICATIONS

"Effects of Electron Radiation Generated during E-beam Evaporation on a Photoresist Liftoff Process," Kezia Cheng et al., International Conference on Compound Semiconductor Manufacturing Technology (CS MANTECH), May 17-20, 2010.

"Reduction of nodules in electron-gun-evaporated Au films," L.G. Feinstein and M. J. Bill, Journal of Vacuum Science & Technology, vol. 12, No. 3, May/Jun. 1975.

Power Point Presentation of "Effects of Electron Radiation Generated during E-beam Evaporation on a Photoresist Liftoff Process" presented by Kezia Cheng at the CS Mantech Conference, May 17-20, 2010.

* cited by examiner

ELECTRON RADIATION MONITORING SYSTEM TO PREVENT GOLD SPITTING AND RESIST CROSS-LINKING DURING EVAPORATION

RELATED APPLICATIONS

This application claims the benefit under 35 U.S.C. §120 as a continuation of U.S. application Ser. No. 12/831,855 titled "ELECTRON RADIATION MONITORING SYSTEM TO PREVENT GOLD SPITTING AND RESIST CROSS-LINKING DURING EVAPORATION," filed on Jul. 7, 2010, which claims priority under 35 U.S.C. §119(e) to U.S. Provisional Application Ser. No. 61/303,040, titled "ELECTRON RADIATION MONITORING SYSTEM TO PREVENT GOLD SPITTING AND RESIST CROSS LINKING DURING EVAPORATION," filed on Feb. 10, 2010, each of which are herein incorporated by reference in their entireties.

BACKGROUND

1. Field of Invention

The present disclosure relates generally to metal deposition systems and, more specifically, to systems and methods for the detection and/or rectification of conditions caused by impurities in metal evaporation sources used in electron-beam metal evaporation/deposition.

2. Discussion of Related Art

Various steps in the processing of semiconductor wafers to form microchips for use in electronic devices involve the deposition of one or more layers of metal on the semiconductor wafers. These metal films are used to form, for example, metal contacts or conductive pathways. Metal films are deposited on semiconductor wafers generally through the use of either chemical vapor deposition (CVD) systems or physical vapor deposition (PVD) systems. PVD systems are generally divided into sputtering systems and evaporation systems.

In sputtering systems, an energetic beam of ions, for example, argon ions, is directed at a metal target in a vacuum chamber. The energetic ions knock metal atoms free from the target. The freed metal atoms travel through the vacuum chamber and deposit on one or more wafers also present in the vacuum chamber.

In evaporation systems (also referred to herein as evaporation/deposition systems), a metal source (also referred to herein as a metal slug) is heated in a vacuum chamber, maintained at about $10^{-7}$ Torr in some systems, until the metal melts and atoms evaporate from the metal source. The metal source may be heated by any of a number of methods, including, for example, resistive heating or by directing an electron-beam into the metal source. The metal atoms evaporated from the metal source travel through the vacuum chamber and deposit on one or more semiconductor wafers also present in the vacuum chamber.

During the deposition of metal onto a semiconductor wafer, in accordance with some semiconductor manufacturing processes, the semiconductor wafer may be covered by a blocking material, conventionally referred to as a "mask," on areas of the wafer in which it is desired that a metal film not be formed. The mask may be formed from, for example, a patterned layer of photoresist (also referred to herein as "resist"). Open areas in the mask are formed where it is desired that the metal film be deposited onto the wafer. These open areas may be formed by, for example, applying a layer of photoresist to a wafer and exposing the photoresist to light which has passed through a lithography mask including a pattern desired to be formed in the photoresist. The photoresist exposed to the light becomes polymerized. A subsequent development step chemically removes non-polymerized photoresist. The remaining photoresist is baked to remove volatile chemicals. Desirably, the remaining photoresist is polymerized, but not cross-linked, i.e., hardened. Aspects and embodiments of the methods and apparatus disclosed herein are not limited to semiconductor manufacturing processes using any particular mask formation process.

After deposition of the metal film, the mask is removed, taking with it any metal that was deposited on the mask, a process known as metal lift-off. What is left behind is a metal film formed in the areas on the semiconductor wafer that were not blocked by the mask.

In some semiconductor manufacturing processes, metallized wafers are put through a wet strip process in a solvent such as N-Methyl Pyrrolidone (NMP) or ethylene glycol to dissolve photoresist that was used as a mask to define the desired metallization pattern, liftoff the unwanted metal(s), and to form a desired portion of an electrical circuit.

Most available photoresists can be cross-linked if exposed to excessive heat or light. Cross-linked or hardened photoresist will not dissolve completely in the normal wet strip chemicals used in some manufacturing processes. A photoresist residue will thus remain on a wafer after the stripping process if the photoresist on the wafer became cross-linked prior to the stripping process. Although the photoresist residue can usually be removed by reworking using more aggressive wet and/or dry strip to processes, the additional rework steps negatively impact the production flow and manufacturing schedule.

Further, if contamination present on a semiconductor wafer, such as photoresist residue or nodules from metal "spitting," discussed below, are not detected on the wafer, this contamination may lead to further problems with downstream processing steps. Such problems may include, for example, poor adhesion or planarity of subsequently deposited layers. These problems may result in a reduction in line yield (the amount of wafers that are not scrapped during manufacturing) and/or die yield (the amount of functional devices per wafer formed in the manufacturing process). Undetected contamination may also lead to reliability problems including failure of a device in the field.

SUMMARY

This Summary is provided to introduce a selection of concepts in a simplified form that are further described below in the Detailed Description. This Summary is not intended to identify key features or essential features of the claimed subject matter, nor is it intended to limit the scope of the claimed subject matter.

Applicant has discovered that some photoresists may be cross-linked not only by exposure to heat or light, but also by bombardment with backscattered electrons from an electron-beam used to heat a metal slug in an evaporator. Further, the Applicant has found that the amount of cross-linking and metal "spitting" is related to the amount of impurities in the metal slug.

In accordance with an embodiment of the present invention, there is provided a method of detecting impurities in a metal slug disposed in an electron-beam evaporator during an electron-beam metal evaporation/deposition process. The method comprises monitoring, during the electron-beam metal evaporation/deposition process, a first electrical signal provided by an electrode that is located in a deposition chamber of the electron-beam evaporator and physically displaced from the metal slug, detecting a change in the first electrical signal during the electron-beam metal evaporation/deposition process, and responsive to the detected change in the first electrical signal, indicating an increased impurity concentration in the metal slug.

In accordance with some aspects, the act of detecting comprises comparing the first electrical signal to a threshold value, and determining that impurities above a defined concentration are present in the metal slug in response to the first electrical signal exceeding the threshold value by more than a predetermined amount.

In accordance with some aspects, the threshold value is determined by monitoring, over a period of time of the electron-beam metal evaporation/deposition process, a second electrical signal provided by the electrode, wherein the threshold value is determined from the second electrical signal.

In accordance with some aspects, monitoring at least one of the first electrical signal and the second electrical signal comprises at least one of monitoring a reading of a voltage and monitoring a reading of a current. In accordance with further aspects, monitoring at least one of the first electrical signal and the second electrical signal comprises monitoring at least one of a first series of periodic readings and a second series of periodic readings, respectively. In accordance with further aspects, the method further comprises establishing a baseline mean value and a baseline standard deviation for the second series of periodic readings. In accordance with further aspects of the method, determining that impurities above the defined concentration are present in the metal slug at above a defined concentration comprises making the determination in response to at least one of an observation of the first series of periodic readings from the electrode having a mean value shifted by more than a predetermined amount from the baseline mean value and an observation of the first series of periodic readings from the electrode having a standard deviation shifted by more that a predetermined amount from the baseline standard deviation. In accordance with further aspects, the method further comprises providing the first series of periodic readings and the second series of periodic readings to a computer system programmed to generate an alarm in response to the first series of periodic readings violating a set of statistical process control (SPC) rules established based upon the second set of periodic readings.

In accordance with some aspects, the method further comprises providing, in response to the determination that impurities are present in the metal slug at above a defined concentration, an indication to a production control system that the electron-beam metal evaporation/deposition system is unfit for processing semiconductor product wafers.

In accordance with some aspects, the method further comprises directing an electron-beam to a surface of the metal slug wherein the acts of monitoring the first and second electrical signals include monitoring backscattered electrons from an impact of the electron-beam with impurities in the metal slug. In accordance with further aspects, the method further comprises providing for an alteration in at least one of a voltage of the electrode and a current flowing from the electrode by providing for the backscattered electrons to impact the electrode.

In accordance with some aspects, the method further comprises, responsive to a determination that impurities above a defined concentration are present in the metal slug, replacing the metal slug.

In accordance with another embodiment of the present invention, there is provided a method. The method comprises depositing, in a vacuum chamber of an electron-beam metal evaporation/deposition system, metal obtained from a metal slug during an electron-beam metal evaporation/deposition process on a semiconductor wafer, monitoring an electrical signal, provided by an electrode located in the vacuum chamber during the electron-beam metal evaporation/deposition process, detecting a change in the electrical signal during the electron-beam metal evaporation/deposition process, and responsive to the detected change in the electrical signal being indicative of an increased impurity concentration in the metal slug, at least one of halting processing of semiconductor wafers on the electron-beam metal evaporation/deposition system and performing preventative maintenance on the electron-beam metal evaporation/deposition system.

In accordance with some aspects, the method further comprises inspecting semiconductor wafers that were being processed in the electron-beam metal evaporation/deposition system at the time of the detected change in the electrical signal. In accordance with further aspects, the method further comprises reworking the semiconductor wafers that were being processed in the electron-beam metal evaporation/deposition system at the time of the detected change in the electrical signal.

In accordance with some aspects, the method further comprises electrically isolating the electrode from ground.

In accordance with some aspects, performing preventative maintenance comprises replacing the metal slug.

In accordance with some aspects, monitoring an electrical signal provided by the electrode during the electron-beam metal evaporation/deposition process comprises monitoring an electrical signal generated by electrons backscattered from impurities in the metal slug on the electrode.

In accordance with some aspects, an increase in yield is achieved by reducing the number of semiconductor wafers comprising photoresist cross-linked during processing in the electron-beam metal evaporation/deposition system.

In accordance with some aspects, an increase in yield is achieved by reducing the number of semiconductor wafers comprising metal nodules produced by metal spitting during processing in the electron-beam metal evaporation/deposition system.

In accordance with another embodiment of the present invention, there is provided an electron-beam metal evaporation/deposition system. The electron-beam metal evaporation/deposition system comprises an electrode configured to be positioned within a vacuum chamber of the electron-beam metal evaporation/deposition system and isolated from ground, the electrode configured to be positioned such that there is an unobstructed straight line path between a portion of the electrode and a surface of the metal slug during operation of the electron-beam metal evaporation/deposition system, the electrode further being configured to be positioned so as not to obstruct a straight path between the surface of the metal slug and a wafer positioned for processing in the electron-beam metal evaporation/deposition system, and an electrical meter coupled to the electrode.

In accordance with some aspects, the electrical meter is at least one of a voltage meter and a current meter.

In accordance with some aspects, the apparatus further comprises a controller configured to receive a signal from the electrical meter, to detect a change in the signal from a baseline, and to alert an operator to the change in the signal.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
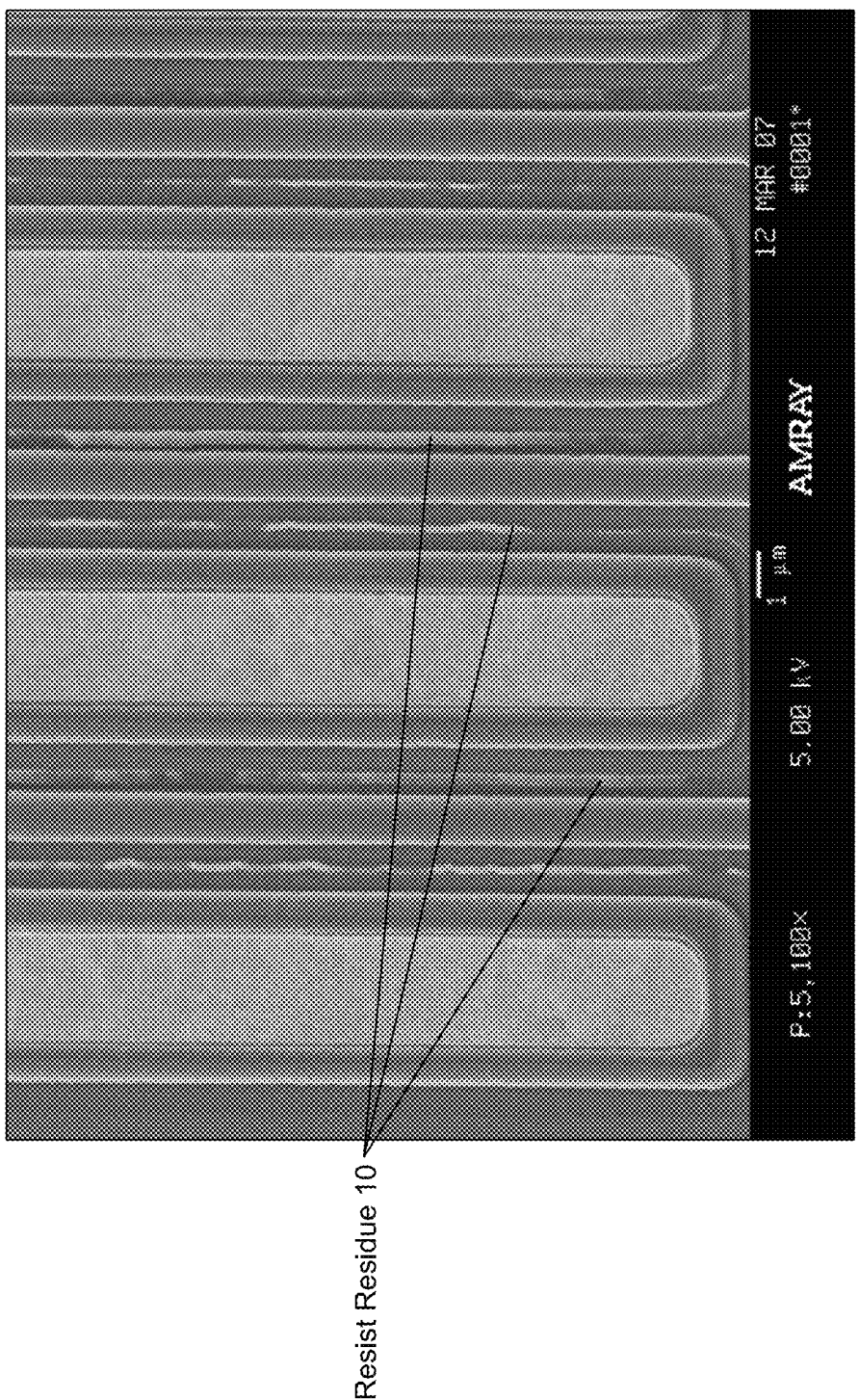
FIG. 1 is a scanning electron microscope (SEM) image of photoresist residue on a surface of a semiconductor wafer.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof, is meant to encompass the items listed thereafter and equivalents thereof as well as additional items.

The present disclosure is directed generally to systems and methods for detecting impurities in metal slugs used in electron-beam (e-beam) metal evaporation/deposition systems (also referred to herein as "evaporators," "e-beam evaporators," or "metal evaporators.") It is desirable to detect impurities in these metal slugs before processing many wafers through an evaporator fitted with a contaminated metal slug. The impurities are a cause of numerous forms of defects that may be observed on wafers processed through an e-beam metal evaporation/deposition system or which may not be immediately observable, but may lead to failures during subsequent processing steps or in the field.

For example, impurities such as carbon may be present in gold slugs. Carbon can be incorporated during the drawing and swaging process of the gold slug manufacturing where oil is used as a lubricant. Poor clean room practice and improper handling techniques while replacing a gold slug in an evaporator can also introduce carbon to the gold slug.

Figure 2:
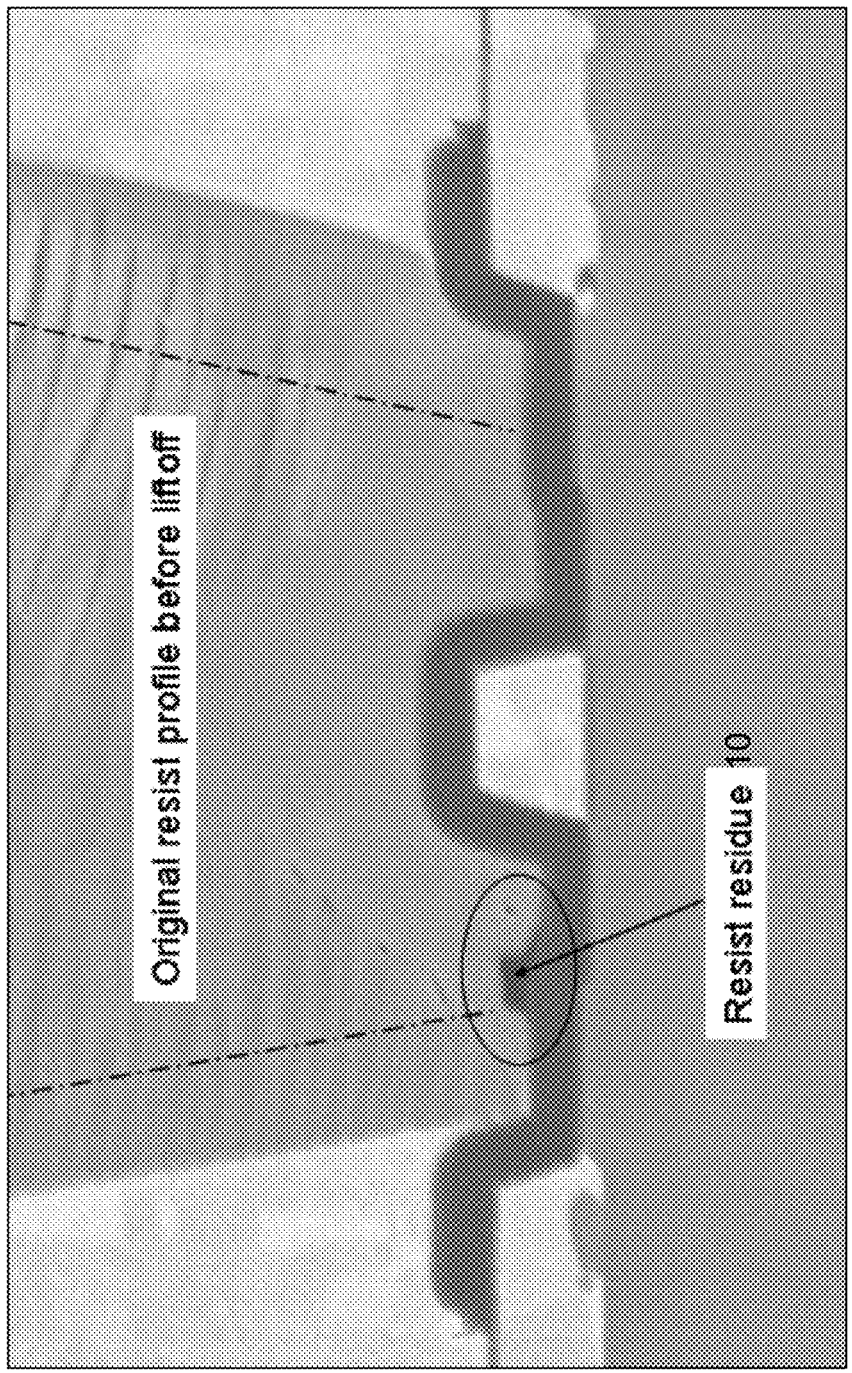
FIG. 2 is a SEM image of photoresist residue in a cross section of a semiconductor wafer.

Impurities such as carbon in a gold metal slug will cause high-energy backscattered electrons to be generated when the metal slug is heated by an e-beam to evaporate the gold. These backscattered electrons may strike areas of photoresist on wafers being processed in the e-beam metal evaporation/deposition system, and cause the photoresist to cross-link. The cross-linked photoresist may, as described above, not be completely removed in a subsequent photoresist stripping process, leaving behind a photoresist residue that requires reworking and/or additional cleaning of the wafer to remove. Examples of photoresist residues 10 formed on semiconductor wafers according to this mechanism are illustrated in FIGS. 1 and 2.

An electron-beam striking a molten metal slug will also generate an emission of secondary electrons from the metal slug. The secondary electrons are formed from electrons in the electron-beam knocking electrons free from atoms in the metal slug or from electrons in the electron-beam being absorbed and then re-emitted from an atom in the metal slug. The secondary electrons typically have energies far below that of the backscattered electrons, and thus do not contribute to photoresist cross-linking as much as the backscattered electrons, if at all.

Carbon impurities in a molten gold slug float to the surface of the molten slug forming a "skin." When an electron-beam directed to the surface of the gold slug encounters the carbon, some of the electrons from the electron-beam are elastically backscattered. Backscattered electrons do not efficiently transfer their energies to the gold slug to melt the gold. The backscattered electrons typically retain most, if not all of the energy that was imparted to them in the formation of the electron-beam. The energy of the backscattered electrons is about 10 kilovolts in a typical e-beam metal evaporator system. If backscattered electrons reach a portion of photoresist on a wafer being processed in an e-beam metal evaporation/deposition system in sufficient number, they may impart sufficient energy to the photoresist to cause the portion of the photoresist to become cross-linked.

The exact reason why carbon particles in a molten gold slug tend to back scatter electrons from an applied electron-beam is not fully understood. It has been discovered, however, that a material in a solid phase generates significantly more free electrons when struck by an electron-beam than when it is in a liquid phase. When the electron-beam hits a solid source, it generates many energetic electrons. When the source is molten the emission level drops. Because of its very high melting point, carbon remains in solid form in a molten gold slug at the temperatures typically used in e-beam metal evaporation/deposition systems, and thus may effectively block the electron-beam from reaching and melting the gold in the slug, causing electrons to elastically back-scatter rather than to be absorbed into the gold slug.

Sidewalls of patterned photoresist used as a mask for a metal deposition process are exposed during the entire deposition process, whereas the surface of the photoresist is shielded as it becomes covered in metal as the metal deposition process proceeds. The photoresist under large metallized features will be shielded from further bombardment by backscattered electrons once the first several hundred angstroms of metal is deposited. The photoresist sidewalls will thus be cross-linked more than the surface of the photoresist. This leads to a line-like or stringer pattern of photoresist residue after the remaining photoresist is chemically stripped, as is illustrated in FIG. 1.

Carbon impurities in gold slugs may also contribute to gold "spitting" wherein droplets of liquid gold are ejected from the molten metal slug. These molten droplets may deposit onto wafers being processed in the e-beam metal evaporation/deposition system and may in some cases cause shorts between adjacent metal lines or other structures on devices being formed on the wafer. For example, gold "spit" on an inside surface of an electrode of a metal-insulator-metal (MIM) capacitor can cause reliability problems. The gold particles deposited by gold "spitting" can also damage probe needles or expensive membrane probes used in testing of the microchip circuitry.

In some semiconductor manufacturing processes, an attempt is made to reduce defects caused by carbon impurities in gold slugs used in gold evaporators by adding tantalum to the gold slug. The tantalum getters carbon, thereby reducing the amount of carbon that is free to form a film on the surface of the melted slug and cause "spitting" or electron back scattering. This approach, however, is not problem-free. Crucibles used in e-beam evaporators for holding gold (or other metal) slugs are typically formed from materials such as, for example, molybdenum, tungsten, silicon carbide, or carbon. Addition of tantalum to the gold slug can induce wetting of a crucible holding the gold slug. If a crucible becomes wetted by molten gold, the crucible may crack due to differential thermal contraction between the material of the crucible and the gold upon cooling. Further, the addition of tantalum to the gold slug does not in all instances result in a spit-free process. Thus, it would be desirable to provide for the identification of a contaminated slug prior to it causing defects on a significant number of wafers, rather than to attempt to mitigate the effects of potential contaminants by, for example, the addition of gettering materials to the metal slug.

Figure 3:
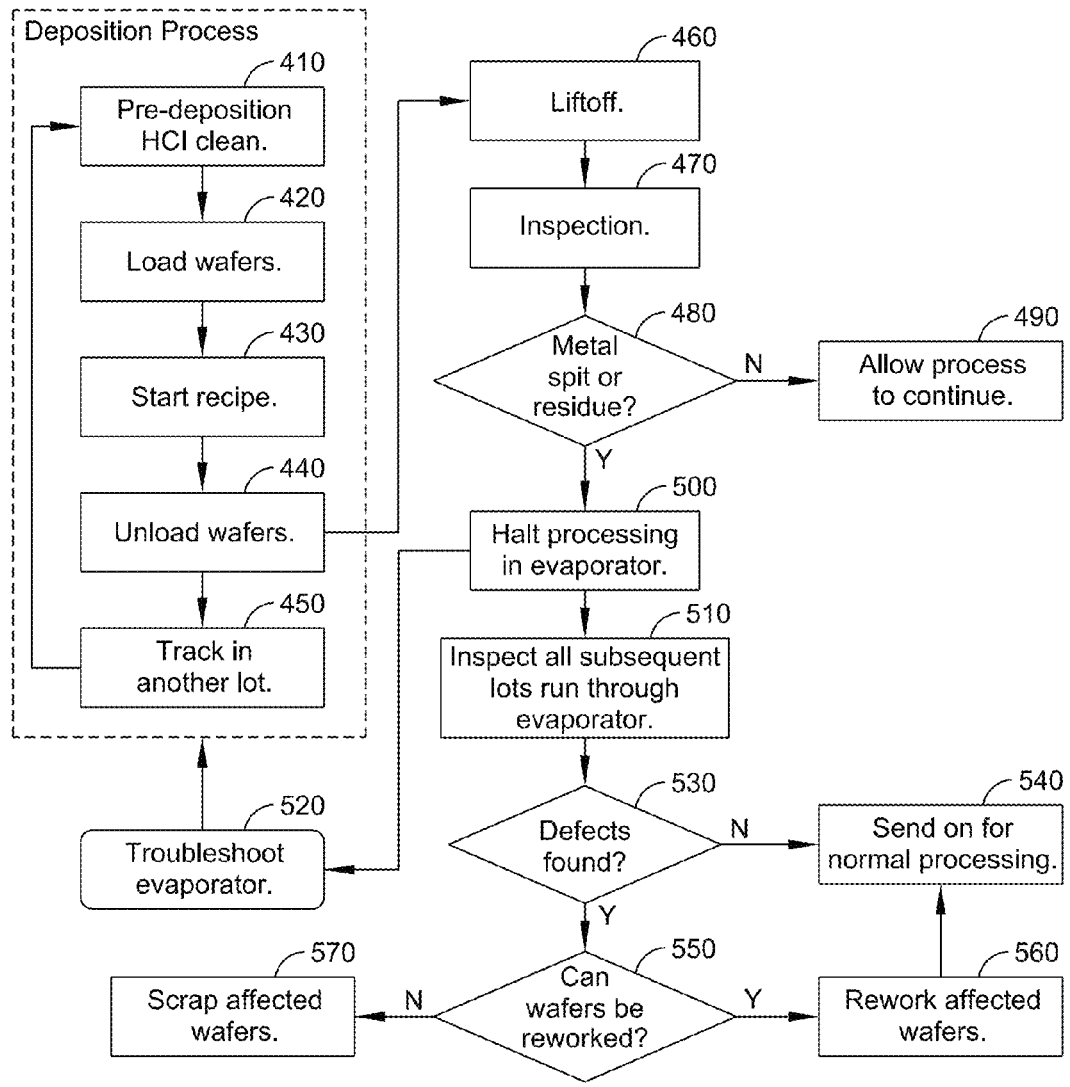
FIG. 3 is a flowchart of a portion of a conventional semiconductor manufacturing process flow.

A typical semiconductor manufacturing process will generally include a series of process steps similar to those illustrated in the flowchart of FIG. 3. A metal deposition process typically includes the acts 410-450 in FIG. 3. In step 410 wafers are cleaned by, for example, immersing them in an acid solution such as hydrochloric acid. After the pre-deposition clean, the wafers are loaded into a metal evaporator (act 420) and a metal deposition recipe is run (act 430). Upon completion of the metal deposition, the wafers are removed from the metal evaporator (act 440) and another lot of pre-cleaned wafers is introduced into the evaporator (act 450).

The wafers that received the metal deposition undergo a lift-off process (act 460) wherein photoresist and/or another metal deposition mask which may have been used is removed from the wafers, along with metal that deposited on the mask. The wafers then typically proceed to an inspection operation (act 470) where inspection of a portion, or in some processes, all of the wafers, is performed by, for example, an automated optical inspection tool. In some processes, the inspection operation is performed manually. During the inspection operation 470 it is determined whether defects such as resist residue or metal "spit" nodules are present on the processed wafers (act 480). If less than a predetermined amount of defects are observed, the processed wafers are sent on to further processing operations and the processing of wafers in the evaporator continues (act 490).

If, however, an unacceptable number of defects are observed on inspected wafers, the evaporator is taken out of service (act 500) and troubleshot (act 520). Wafers processed through the metal evaporator subsequent to a lot which was discovered to include wafers having defects from the metal deposition process would be suspect. If the defects discovered in the first bad lot were indeed caused by a problem such as contamination of the metal slug in the evaporator, it would be highly likely that lots processed subsequent to the first discovered bad lot would also exhibit defects due to the contaminated metal slug. These lots would thus also most likely need to be reworked or scrapped. A sample, or in some instances all, wafers that were processed through the evaporator subsequent to the wafers which were determined in act 480 to have an unacceptably high amount of defects are thus inspected (act 510).

A determination is made if these subsequently run wafers also exhibit unacceptable levels of defects (act 530). If the wafers appear to be acceptable, they are sent on for normal further processing (act 540). If, however, these wafers show unacceptably high levels of defects, a determination is made whether they may be reworked (act 550) by, for example, an additional cleaning operation to remove observed resist residue.

If the wafers are determined to be reworkable, they are reworked (act 560) and then sent on for further processing (act 540). In some instances, the reworked wafers would be inspected again prior to being sent on for further processing. If in act 560 it is determined that the wafers are not reworkable, for example if they have an unacceptably high level of non-removable metal "spit," then the wafers are scrapped (act 570.)

In a typical semiconductor manufacturing process, many lots of wafers may be processed through a metal evaporator between the time a bad slug begins to cause the appearance of defects on wafers processed therethrough and the time that these defects are discovered at a downstream inspection step. Many lots of wafers may be affected before the problem with the metal slug is discovered. A contaminated slug can thus cause a significant cost to be incurred in terms of time and production capacity to rework wafers to, for example, remove resist residue. A significant cost may also be incurred if the defects found on the wafers cannot be remedied by a rework process, and the affected wafers must be scrapped.

To facilitate a reduction in these potential losses, a method and apparatus has been developed to detect the presence of a contaminated metal slug in an evaporator in less time than in previously known processes, and in some embodiments, in real-time during operation of the evaporator. It has been discovered that by fabricating an electrode 510 (see FIGS. 4 and 5) to fit inside an evaporator deposition chamber 505, the overall electron radiation emerging from a metal slug (for example, a gold slug) during operation of the evaporator may be monitored. In some embodiments, the electrode 510 is electrically isolated from the interior surfaces 515 of the evaporator and from ground 550 by one or more insulating standoffs 520. In some embodiments, the electrode is electrically coupled to a high impedance voltmeter 710 and/or current meter (see FIG. 6).

In some embodiments, the electrode 510 and/or the insulating standoffs 520 would be cleaned or replaced along with other miscellaneous pieces of evaporator shielding during regularly scheduled preventative maintenance operations.

During operation, an e-beam 537 is generated by an electron gun 535 and directed to the metal slug in the crucible 530. Electrons generated by the e-beam 537 striking the metal slug will be backscattered and impact the electrode 510, inducing a negative voltage and/or a current from the electrode. The measured voltage would be proportional to the amount of backscattered electrons generated, and thus, the amount of impurities in the metal slug, for example carbon impurities on a gold slug. The higher the carbon concentration in a gold slug, the more negative the voltage on the electrode. Similarly, the higher the carbon concentration in a gold slug, the more backscattered electrons impact the electrode, and the greater the current generated. When the amount of carbon on the gold slug has reached a threshold value, as indicated by the voltage of the electrode and/or a current generated by the electrode, resist cross-linking and/or gold spitting will occur. Thus, the voltage on the electrode and/or the current generated from the electrode can be monitored and the evaporator shut down for replacement of the metal slug when the voltage and/or current approaches or exceeds a threshold value. The voltage generated on the electrode would in some embodiments be a negative voltage, so to exceed a threshold voltage would be to display a voltage that is more negative than a threshold negative voltage.

As described above, without detection of the impurity or impurities in the metal slug during the metal deposition process, problems (for example, gold spitting and/or resist cross-linking) may go undetected for many runs until the affected wafers reach inspection much later in the manufacturing process. This could result in many scrapped lots and lost revenue. Some embodiments of the present invention can identify the cause of these problems as soon as it begins to appear.

Embodiments of the present invention can provide an indication to an operator of when to change a metal source in an evaporator. In some embodiments, this indication is given prior to the occurrence of problems such as resist cross-linking and/or metal spitting. By monitoring the electrode potential, or in some embodiments, current, one can establish a proper threshold voltage or current that would indicate desirability for a prompt replacement of a contaminated metal slug.

Figure 4:
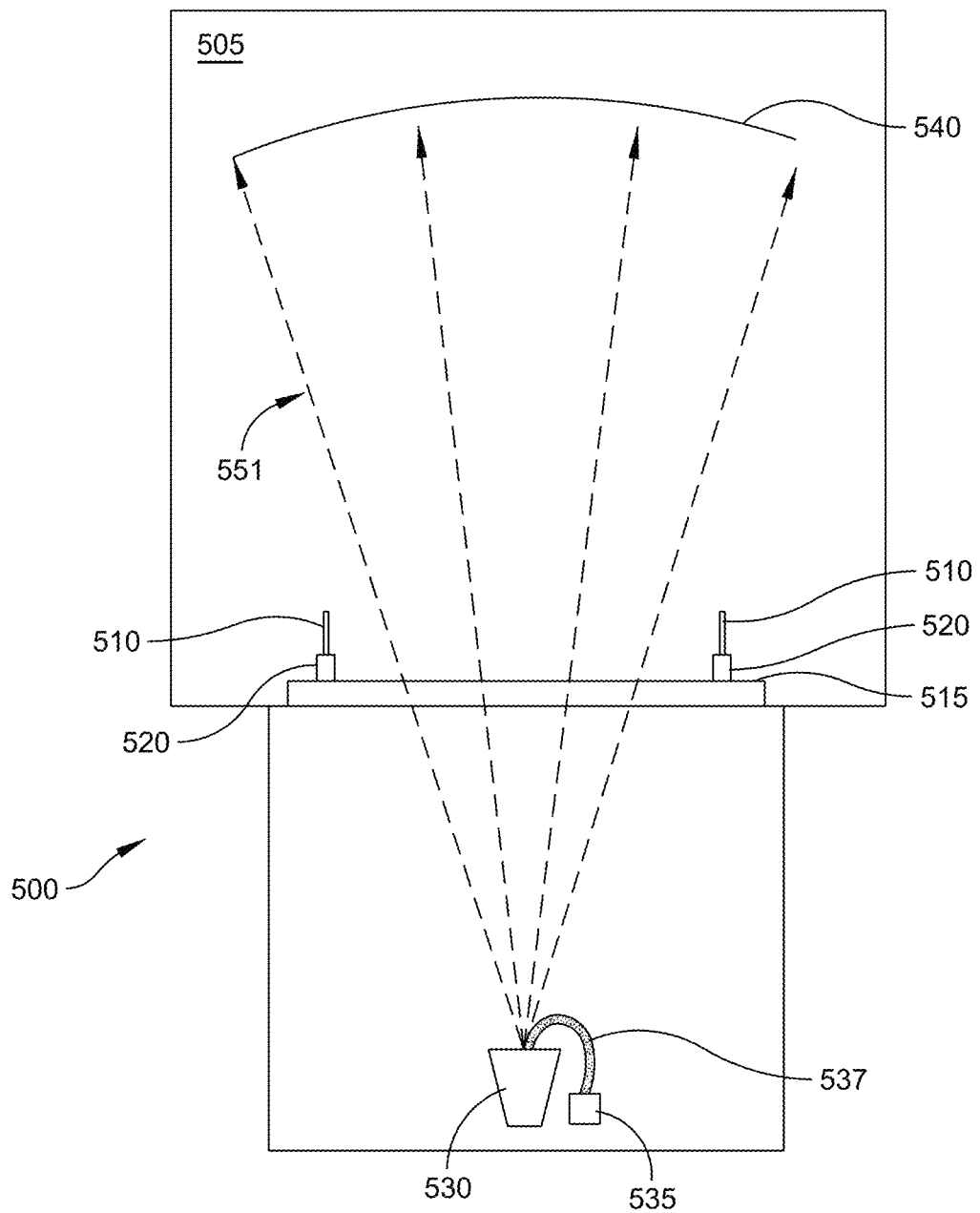
FIG. 4 is a cross sectional illustration of an electron-beam metal evaporation/deposition system including an electrode in accordance with an embodiment of the present invention.
Figure 5:
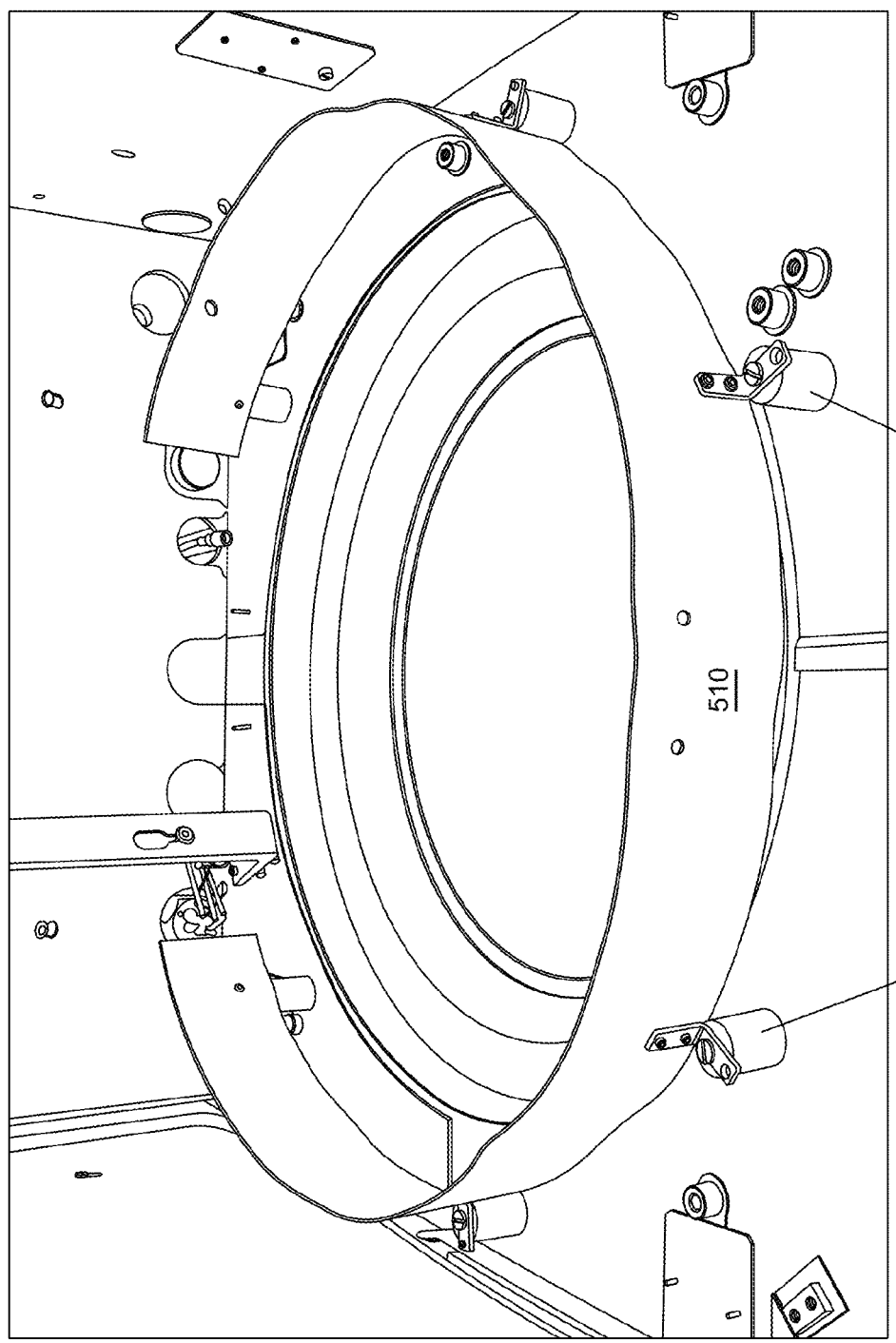
FIG. 5 is a photograph of the electrode of FIG. 4 mounted in a deposition chamber of an electron-beam metal evaporation/deposition system.
Figure 6:
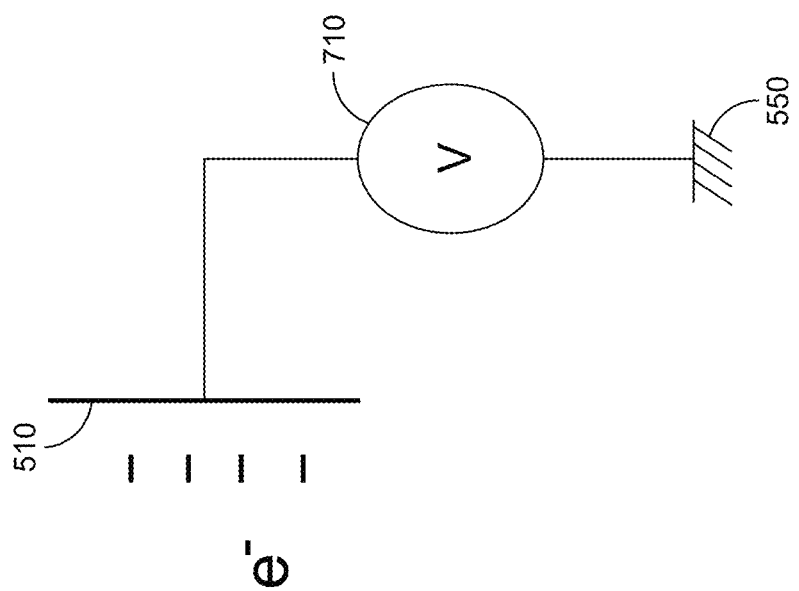
FIG. 6 is a schematic of an electrical meter electrically coupled to an electrode in accordance with an embodiment of the present invention.

As illustrated in FIGS. 4 and 5, in one embodiment, the electrode 510 is fabricated in the form of a ring of copper plating. There are two reasons for using copper as an electrode material. First, copper is a very good conductor. Second, copper is a metal that is compatible with high vacuum systems. However, any conductive metal that is vacuum compatible (for example, stainless steel) can be used in a commercial system, as the present invention is not limited to a particular type of electrode material.

The insulating standoffs 520 isolating the electrode 510 from the internal surfaces 515 of the evaporator and from ground are, in one embodiment, constructed from aluminum oxide, an insulating ceramic material. In other embodiments, the insulating standoffs 520 are constructed of other ceramics such as titania, silicon dioxide (quartz), or conventional glass. In other embodiments, the standoffs 520 are formed from a plastic material such as PVDF. Any non-conductive material that is vacuum compatible and has sufficient mechanical strength to support an electrode may be utilized for the standoffs 520.

In the embodiment illustrated in FIGS. 4 and 5, the electrode 510 is placed in the evaporator deposition chamber 505 such that when the evaporator is in operation, there is an obstruction-free path between the electrode 510 and a metal slug contained within a crucible 530 within the evaporator. The electrode 510 is also positioned such that it does not obstruct a path 551 between the metal slug and positions on a wafer support structure 540 where wafers would be mounted during metal deposition in the evaporator. This positioning of the electrode provides for the electrode to collect backscattered (and secondary) electrons from the metal slug, but to not block metal from being deposited on wafers.

Although illustrated as a ring of copper plating, the electrode may, in alternate embodiments, be formed in any number of shapes and configurations. For example, in one embodiment, the electrode is in the form of one or more rings of wire. In another embodiment, the electrode is formed from a plurality of plates within the evaporator deposition chamber. In a further embodiment, the electrode 510 is formed from a metal screen. The skilled artisan would be able to form the electrode 510 in any of a number of shapes and sizes to fit within any particular model of evaporator.

In operation, a voltage and/or a current generated on the electrode 510 during the operation of an evaporator using a known good metal slug is monitored to establish a baseline level for the voltage and/or current. Multiple voltage and/or current data points are taken over time at a given frequency, for example, one data point every half second, or in some embodiments, one data point per second. Other embodiments could use a data sampling frequency at any rate that is convenient or within the capabilities of data logging equipment utilized in conjunction with the electrode. These data points are used to generate a baseline mean value, a baseline range or standard deviation, or in some embodiments, both a baseline mean and standard deviation or range for one or both of voltage and current generated from the electrode during operation of the evaporator with a known good metal slug.

Embodiments of the present invention may be utilized to detect impurities in multiple types of metal slugs, for example, gold, aluminum, titanium, or any other metals that may be used in a metal evaporator. These different metals will generate different amounts of backscattered and secondary electrons when struck by an e-beam. The amount of backscattered and secondary electrons generated will also vary depending on the particular model of evaporator used and the intensity of the e-beam applied to the metal slug. Further, the particular design, shape, positioning, and material or materials of construction of a particular electrode will affect the amount of electrons the electrode would capture. Thus, a baseline in voltage and/or current generated for a particular type of metal slug on a particular evaporator with a particular electrode configuration will generally not be the same as a baseline generated on a different evaporator with a different type of metal slug and/or electrode configuration. However, differences between an established baseline in voltage and/or current generated for a clean metal slug and a shift in this baseline indicative of a contaminated slug can be detected regardless of the particular value(s) of baseline parameter(s) established.

An established baseline may also vary from one metal slug to another on the same evaporator due to, for example, buildup of metal on the electrode over time, or differences in size, shape, or surface properties of the different metal slugs. An established voltage and/or current baseline for an electrode in an evaporator would, in some embodiments, be periodically recalibrated as a metal slug in the evaporator lost mass due to evaporation, thereby, in some embodiments, increasing a concentration of non-evaporating contaminant material, and/or the electrode accumulated deposited metal.

In other embodiments, the parameters (for example, mean, range, and/or standard deviation) of a voltage and/or current baseline would be substantially the same for different evaporators having similar or the same vacuum chamber and electrode configurations. Thus, in some embodiments, parameters of a voltage and/or current baseline established on one evaporator would be applicable to other similarly configured evaporators. Thus, in some embodiments, there would be no need to establish a voltage and/or current baseline for a particular type of metal slug for each individual evaporator. Rather a voltage and/or current baseline established using a known good metal slug (and, in some embodiments, a known contaminated metal slug) on one representative evaporator would provide the data to establish acceptable thresholds and/or control limits for parameters of electrode voltage and/or current that could be utilized to monitor for the presence of potentially contaminated metal slugs in any of a group of similarly configured evaporators. In some embodiments, a manufacturer of the evaporators would calibrate the evaporators to produce particular parameters of electrode voltage and/or current when running good and contaminated metal slugs. This manufacturer calibration could in some embodiments reduce or eliminate the need for a user of an evaporator to perform baseline measurements to establish control charts for electrical parameters measured on the electrode which could be used to differentiate between good vs. contaminated metal slugs.

Once a baseline in voltage and/or current is established, a deviation in the parameters of this baseline is indicative of potential contamination of a metal slug. For example, a downward shift in voltage and/or an increase in current from the electrode during operation of an evaporator would be indicative of a possible increase in the number of backscattered electrons being generated, and thus of a potentially contaminated source. Similarly, an increase in the standard deviation or range of readings would also, in some embodiments, be indicative of a contaminated metal slug. In some embodiments, an observed voltage signal from an electrode in an evaporator having a particular baseline mean and standard deviation would show both a downward shift in mean and an increase in standard deviation upon contamination of a surface of the metal slug.

Any of a number of other changes in an electrical signal measured on the electrode could be used to provide an indication of a potentially contaminated metal slug. For example, a trend in either the voltage or current readings (i.e. a first derivative of a curve formed from a series of data points) could be indicative of a potentially contaminated slug, if the trend were of a magnitude that was statistically unlikely given the natural variation in the readings. In other embodiments, a change in a moving average of a series (for example, three or five readings in a row) of voltage and/or current readings that was statistically unlikely given the natural variation in the readings could be indicative of a potentially contaminated slug. In further embodiments, a change in a range observed for a series of data points (for example, the last three or five readings in a row compared to a series of previous readings) that was statistically unlikely given the natural variation in the readings could be indicative of a potentially contaminated slug.

One of ordinary skill in the art of process control would be able to set control limits (for example, statistical process control limits) around a set of baseline voltage and/or current readings which when violated, would be an indication of a potentially contaminated metal slug. In some embodiments, control charts for voltage and/or current readings from an electrode would be established and data points for voltage and/or current reading plotted on these control charts. If the plotted data points violated one or more statistical process control (SPC) rules, this would be indicative of a potentially contaminated metal slug.

In some embodiments, control charts could be established and plotted data points monitored for violations of one or more of the Western Electric SPC rules. These rules are as follows:

1) One Point Outside Upper or Lower Control Limits

The Upper and Lower Control Limits are set at three standard deviations from the mean. If a point lies outside either of these limits, there is only a 0.3% chance that this was caused by the normal process.

2) Eight Points on the Same Side of the Mean

There is an equal chance that any given point will fall above or below the mean. The chance that a point falls on the same side of the mean as the one before it is one in two. The odds that the next point will also fall on the same side of the mean is one in four. The probability of getting eight points on the same side of the mean is only around 1%.

3) Eight Points Increasing or Decreasing

The same logic is used here as for "Eight Points on the Same Side of the Mean." Sometimes this rule is changed to seven points rising or falling.

4) Two of Three Points outside Warning Limits

The Warning Limits are usually set at two standard deviations (i.e. two sigma) from the mean. The probability that any point will fall outside the warning limit is only 5%. The chances that two out of three points in a row fall outside the warning limit is only about 1%.

5) Four of Five Points Falling Outside One Sigma

In normal processing, 68% of points fall within one sigma of the mean, and 32% fall outside it. The probability that 4 of 5 points fall outside of one sigma is only about 3%.

6) Fourteen Points Alternating Direction

This rule treats each pair of adjacent points as one unit. The chances that the second point is always higher than (or always lower than) the preceding point, for all seven pairs, is only about 1%.

7) Fifteen Points in a Row within One Sigma

In normal operation, 68% of points will fall within one sigma of the mean. The probability that 15 points in a row will do so is less than 1%.

8) Eight Points in a Row Outside One Sigma

Since 68% of points lie within one sigma of the mean, the probability that eight points in a row fall outside of the one-sigma line is less than 1%.

In other embodiments, control charts could be utilized in which violations of one or more of the Wheeler or Nelson SPC rules (which would be known to those familiar with statistical process control) could be used as an indicator of a potentially contaminated metal slug.

In some embodiments, a voltage and/or current from an electrode in an operating evaporation system is automatically periodically measured by a voltmeter and/or current meter and the measurements fed into a monitoring computer or controller programmed to issue a warning if the measured parameter or parameters drifted above or below a threshold, drifted outside a range deemed acceptable, or violated one or more SPC rules. In some embodiments, an acceptable threshold or range for the measured parameter is previously determined by performing baseline measurements from the electrode on the particular evaporator using the particular metal slug being monitored.

Figure 7:
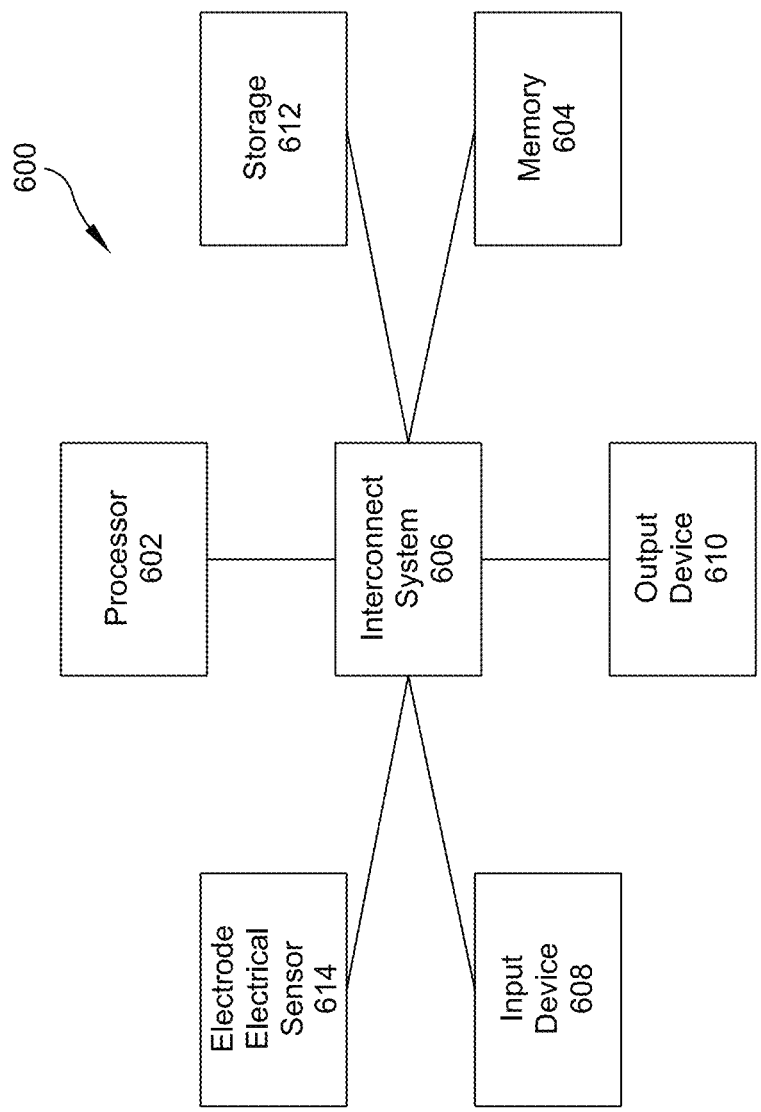
FIG. 7 illustrates a computerized control system which may be utilized in one or more embodiments of the present invention.

In different embodiments, a monitoring computer or controller for monitoring electrical parameters from an electrode 510 may be embodied in any of numerous forms. In one example, a computerized controller for embodiments of the system disclosed herein is implemented using one or more computer systems 600 as exemplarily shown in FIG. 7. Computer system 600 may be, for example, a general-purpose computer such as those based on an Intel PENTIUM® or Core™ processor, a Motorola PowerPC® processor, a Sun UltraSPARC® processor, a Hewlett-Packard PA-RISC® processor, or any other type of processor or combinations thereof. Alternatively, the computer system may include specially-programmed, special-purpose hardware, for example, an application-specific integrated circuit (ASIC) or controllers intended specifically for semiconductor wafer processing equipment.

Computer system 600 can include one or more processors 602 typically connected to one or more memory devices 604, which can comprise, for example, any one or more of a disk drive memory, a flash memory device, a RAM memory device, or other device for storing data. Memory 604 is typically used for storing programs and data during operation of the controller and/or computer system 600. For example, memory 604 may be used for storing historical data relating to measured electrical parameters of an electrode 510 over a period of time, as well as current electrical sensor measurement data. Software, including programming code that implements embodiments of the invention, can be stored on a computer readable and/or writeable nonvolatile recording medium (discussed further with respect to FIG. 8), and then copied into memory 604 wherein it can then be executed by processor 602. Such programming code may be written in any of a plurality of programming languages, for example, Java, Visual Basic, C, C#, or C++, Fortran, Pascal, Eiffel, Basic, COBAL, or any of a variety of combinations thereof.

Components of computer system 600 may be coupled by an interconnection mechanism 606, which may include one or more busses (e.g., between components that are integrated within a same device) and/or a network (e.g., between components that reside on separate discrete devices). The interconnection mechanism typically enables communications (e.g., data, instructions) to be exchanged between components of system 600.

Computer system 600 can also include one or more input devices 608, for example, a keyboard, mouse, trackball, microphone, touch screen, and one or more output devices 610, for example, a printing device, display screen, or speaker. Computer system may be linked, electronically or otherwise, to an electrical sensor 614, which may comprise, for example, one or more of a current meter and a voltage meter configured to measure an electrical parameter of an electrode 510. In addition, computer system 600 may contain one or more interfaces (not shown) that can connect computer system 600 to a communication network (in addition or as an alternative to the network that may be formed by one or more of the components of system 600). This communications network, in some embodiments, forms a portion of a manufacturing process control system for a semiconductor manufacturing line.

According to one or more embodiments, the one or more output devices 610 are coupled to another computer system or component so as to communicate with computer system 600 over a communication network. Such a configuration permits one sensor to be located at a significant distance from another sensor or allow any sensor to be located at a significant distance from any subsystem and/or the controller, while still providing data therebetween.

Figure 8:
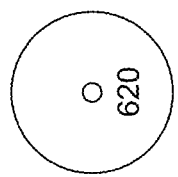
FIG. 8 illustrates a storage system that may be used with the computerized control system of FIG. 7 in accordance with one or more embodiments of the present invention.
Figure 8:
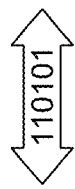
Figure 8:
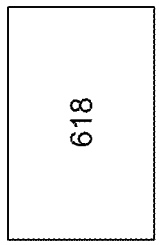
Figure 8:
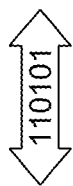
Figure 8:
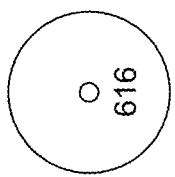

As exemplarily shown in FIG. 8, controller/computer system 600 can include one or more computer storage media such as readable and/or writeable nonvolatile recording medium 616 in which signals can be stored that define a program to be executed by one or more processors 620 (such as processor 602). Medium 616 may, for example, be a disk or flash memory. In typical operation, processor 620 can cause data, such as code that implements one or more embodiments of the invention, to be read from storage medium 616 into a memory 618 that allows for faster access to the information by the one or more processors than does medium 616. Memory 618 is typically a volatile, random access memory such as a dynamic random access memory (DRAM) or static memory (SRAM) or other suitable devices that facilitates information transfer to and from processor 620.

Although computer system 600 is shown by way of example as one type of computer system upon which various aspects of the invention may be practiced, it should be appreciated that the invention is not limited to being implemented in software, or on the computer system as exemplarily shown. Indeed, rather than implemented on, for example, a general purpose computer system, the controller, or components or subsections thereof, may alternatively be implemented as a dedicated system or as a dedicated programmable logic controller (PLC) or in a distributed control system. Further, it should be appreciated that one or more features or aspects of the control system may be implemented in software, hardware or firmware, or any combination thereof. For example, one or more segments of an algorithm executable computer system 600 can be performed in separate computers, which in turn, can be in communication through one or more networks.

Figure 9:
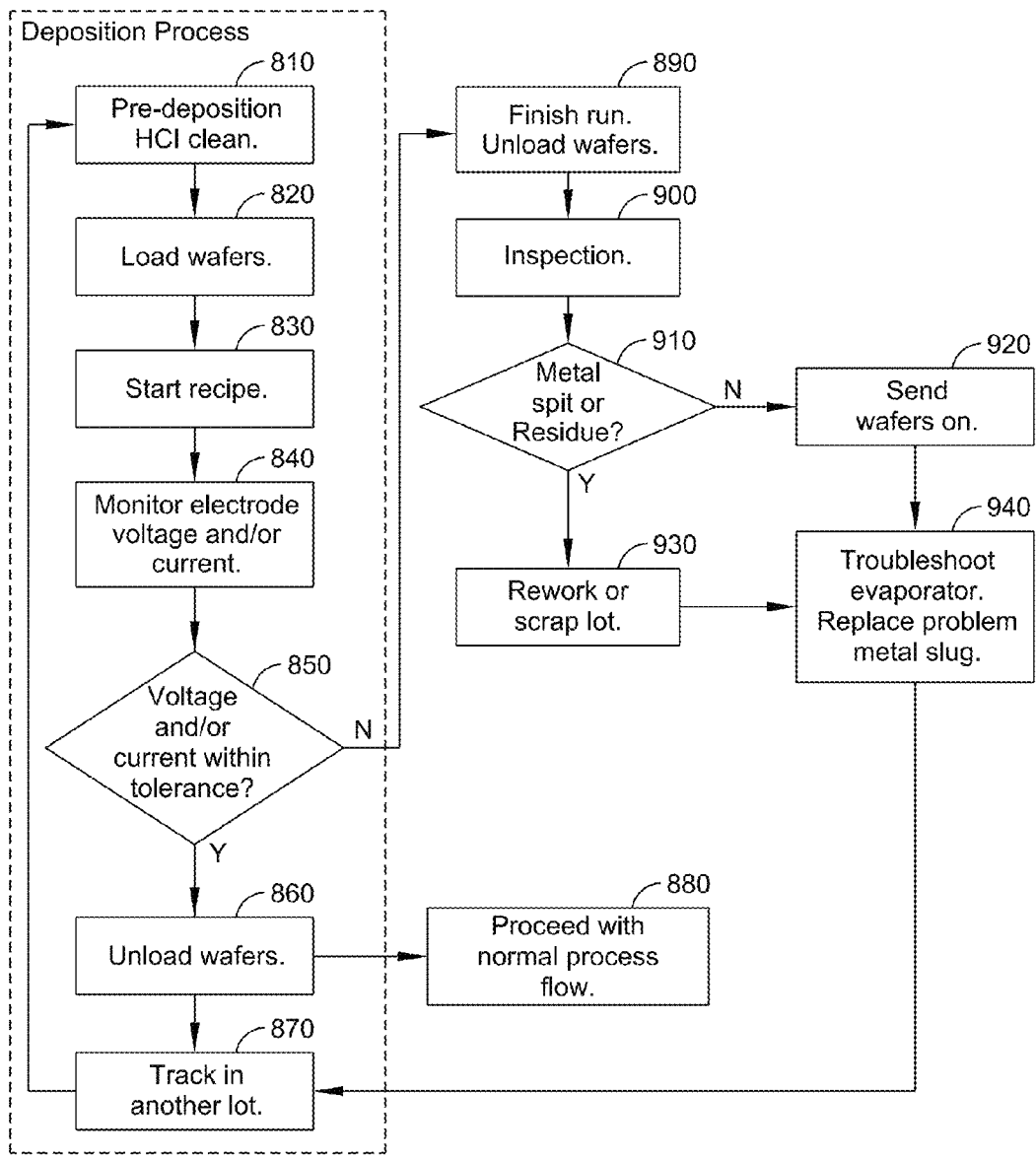
FIG. 9 is a flowchart of a portion of a semiconductor manufacturing process flow in accordance with an embodiment of the present invention.

A process for operating an evaporator including an electrode according to one embodiment of the present invention is illustrated in FIG. 9. In the process of FIG. 9 the deposition operation includes acts 810-870. Acts 810-830 and 860-870 are substantially the same as acts 410-430 and 440-450, respectively, of FIG. 3 described above. In contrast to the process of FIG. 3, the process of FIG. 9 additionally includes an act of monitoring an electrical characteristic of the electrode (act 840). In one embodiment, voltage from the electrode is monitored and a mean and a standard deviation of the monitored voltage are calculated. In another embodiment, current from the electrode is monitored and a mean and a standard deviation of the monitored current are calculated. In act 850, the monitored electrical parameter is compared to a baseline previously established for that parameter and a determination is made as to whether the measured parameter falls within an acceptable tolerance limit.

If it is determined that the measured parameter is within tolerance, the metallization recipe is completed, the wafers are unloaded (act 860) and sent on for normal downstream processing (act 880), and a new lot of pre-cleaned wafers in introduced to the evaporator (act 870). Alternatively, if in act 850, the measured parameter is found to be outside of tolerance, upon unloading of the wafers (act 890), they are sent for inspection (act 900). If it is determined that defects such as metal spit and/or resist residue are present on the wafers at an unacceptable level (act 910) the wafers may be scrapped, or in some embodiments, reworked, if possible (act 930). The evaporator which generated the out of tolerance signal and the defective wafers will be taken out of production and will undergo troubleshooting (act 940). If a metal slug in the evaporator is found to be contaminated it would be replaced prior to bringing the evaporator back on line for continued processing (act 940).

If the wafers that came from the evaporator that displayed the out of tolerance parameter are found to have an acceptably low defect density in act 910, they are sent on for further processing, but as a preventative measure, the evaporator would undergo troubleshooting and any contaminated metal slugs replaced before processing additional product wafers through the evaporator (act 940).

It should be understood that the various acts illustrated in FIG. 9 are exemplary only. In different embodiments, various ones or more of these acts are performed in different orders. In other embodiments, additional acts are included in this process, and in further embodiments one or more of the illustrated acts are omitted or substituted.

Additional embodiments of the method of operation of an evaporator including an electrode as described herein will be apparent to one of ordinary skill in the art. In one alternate embodiment, a positive voltage is applied to the electrode. This positive voltage would attract electrons, thus increasing the amount of electrons captured by the electrode, making the apparatus more sensitive to the presence of backscattered electrons. The positive charge on the electrode would also deflect (at least to some degree) backscattered electrons toward the walls of the deposition chamber and away from the wafers in the wafer support. The amount of deflection would vary with the amount of voltage applied to the electrode. In some embodiments in which a positively biased electrode is utilized, a mean and/or standard deviation of current from the electrode can be utilized as the electrical parameter monitored so that a constant voltage can be maintained on the electrode. In other embodiments, the voltage applied to the electrode is made or allowed to vary over time. As in the above described embodiments, a change in a mean value or standard deviation from a baseline value for the current and/or voltage monitored is indicative of a potentially contaminated metal slug. Upon receipt of a signal from a controller or other system used to monitor the evaporator for an indication of a potentially contaminated electrode, an operator can troubleshoot the evaporator and replace the suspect metal slug if deemed necessary.

In another embodiment, a charge (either positive or negative) can be applied to the electrode 510. The charge on the electrode can be measured over time during operation of the evaporator. A change in the charge or a change in a rate of change in the charge measured on the electrode can be indicative of a potentially contaminated metal slug.

EXAMPLE

To investigate the source of backscattered electron radiation, a series of experiments were conducted to compare the amount of energetic free electrons generated from different materials during the evaporation process in an e-beam metal evaporation/deposition system. An electrode was fabricated to fit inside the vacuum chamber of an e-beam metal evaporation/deposition system vacuum. This electrode provided for the comparison of the number of energetic electrons generated from an electron-beam hitting different materials. The electrode was formed from a copper plate bent into a ring. The copper electrode plate was electrically isolated from ground by ceramic standoffs in the vacuum chamber. A copper wire was utilized to connect the electrode to a high-impedance voltmeter with data-logging capability (a Keithley 2420 source meter), where voltage signals from the electrode were monitored and logged in a data file. Since the set up was not calibrated against any certified standard, the measured potential could not be correlated with an actual amount of charge on the electrode.

A Temescal FC2700 evaporator with a 15 KW power supply was used for this experiment. A recipe with a 30 second ramp up to a 45% constant power delivery cycle used to melt the metal slug and a 30 second ramp to 50% constant power delivery cycle used to maintain the molten slug at a temperature at which metal would evaporate was created. The dwell time was 30 seconds for both constant power cycles. Different gold melts from different gold slugs were run using the recipe while logging the voltage collected at the electrode.

Figure 10:
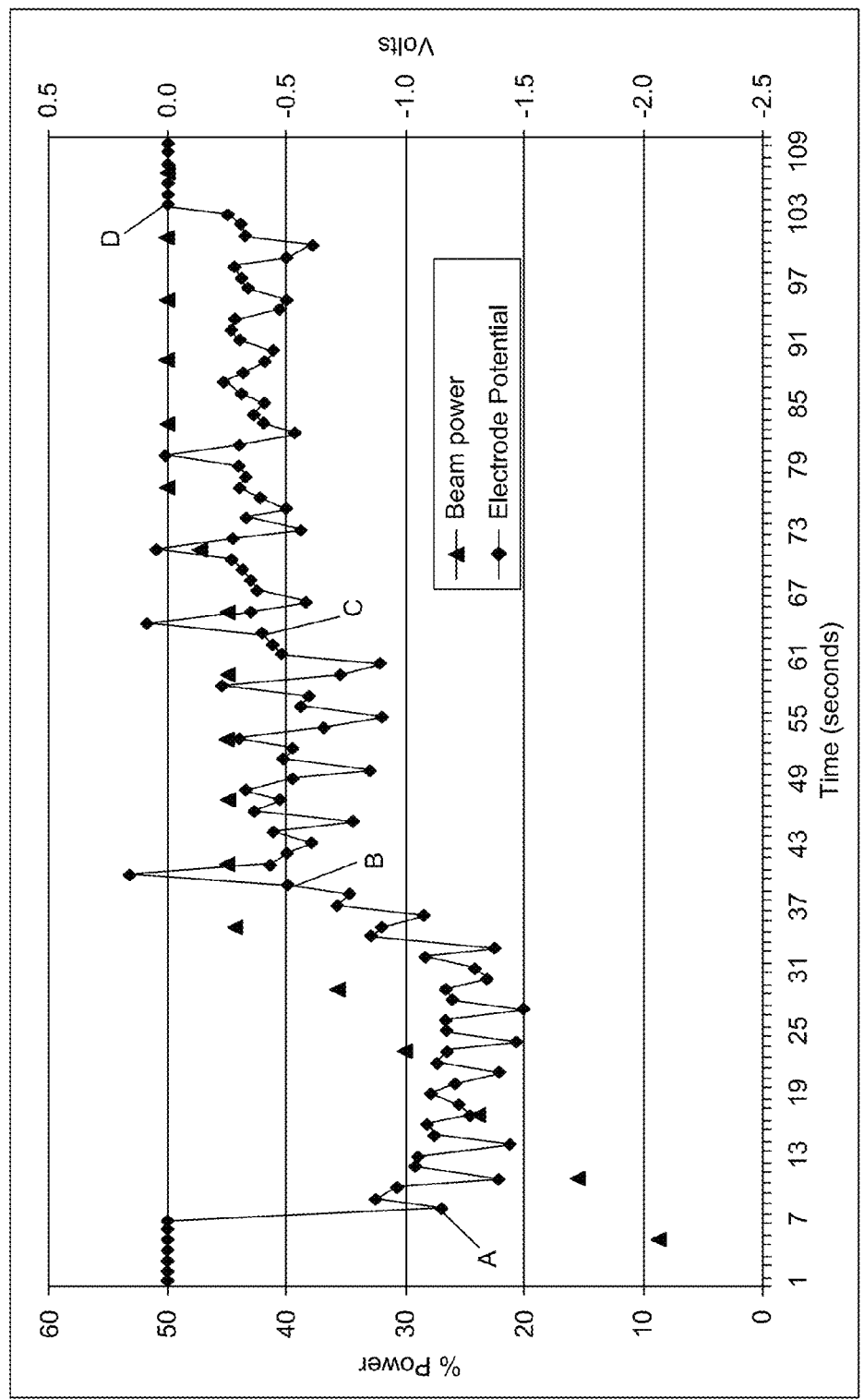
FIG. 10 is a chart of electron-beam power and voltage readings from a test of an electrode according to an embodiment of the present invention mounted in an electron-beam metal evaporation/deposition system.

A first experiment was performed using a gold slug contaminated with an estimated 1 ppm of carbon on the surface. The data obtained from this experiment is illustrated in FIG. 10. In this figure electron-beam power is represented by the "Beam power" data points, and the voltage observed on the electrode is represented by the "Electrode Potential" data points. With the 10 KV high-voltage turned on and the emitter in idle, the electrode potential was 0 V with respect to ground (the portion of the chart to the left of the point indicated at "A.") As soon as there was beam emission current while the power ramped up and the beam started to appear on the gold melt, the SMU measured about −1.25V (the point labeled as "A.") The voltage remained somewhat constant as the power continued to ramp up to 45% of maximum (the data points between the point labeled as "A" and the point labeled as "B.") When the gold slug began to turn molten, the voltage dropped abruptly to −0.5V (the points just prior to the point labeled as "B.") Further increase in power to 50% caused the electrode voltage to fall off to −0.4V (beginning approximately at the point labeled "C.") At point "D" the beam power applied to the gold slug used in the 1 ppm carbon contaminated sample test was abruptly turned off, and the electrode voltage returned to 0 V.

In FIG. 10, the data points for "Beam power" indicate that the beam was still at 50% power at point "D," however, this is an artifact of the data collection methodology. The data for the 1 ppm carbon contaminated sample test and for the 30 ppm carbon contaminated sample test (described below with reference to FIG. 11) were taken during different runs and then merged. The "Beam power" data points correspond more closely in time to the "Electrode Potential" data points for the 30 ppm carbon contaminated sample test, which is why the 30 ppm carbon contaminated sample test data points do not show a return to 0 V at the right hand side of the chart; the beam power was still on during collection of the 30 ppm carbon contaminated sample test data points at the right hand side of the chart.

The melt recipe employed a circular electron-beam sweep pattern of 2 Hz and the sampling rate of the data log was 1 second. The circular sweeping motion of the beam correlated with the spikes in voltages recorded and illustrated in FIGS. 10 and 11. The beam focus changed as the beam swept different parts of the slug's surface. With each pass over the slug, the beam focus tightened when passing over the uncontaminated gold and the beam diffused while passing over areas with high carbon, causing the backscattered electron radiation to vary. When the beam passed over a portion of the gold melt including carbon contamination, a greater amount of electrons were backscattered that when the beam passed over non-contaminated areas of the gold melt. This change in the amount of backscattered electrons when the electron-beam passed over "dirty" v. "clean" areas of the gold melt is reflected in the change in the voltage levels observed in the data points in FIGS. 10 and 11. For the data points corresponding to the 1 ppm carbon contaminated gold melt (FIG. 10), a voltage difference of approximately 0.5 V was observed between data points obtained when the electron-beam passed over a "clean" v. a "dirty" area of the gold melt. For the data points corresponding to a 30 ppm carbon contaminated gold melt (FIG. 11), this voltage difference was about 1 V, about twice the voltage difference observed for the data points corresponding to the 1 ppm carbon contaminated gold melt.

Figure 12:
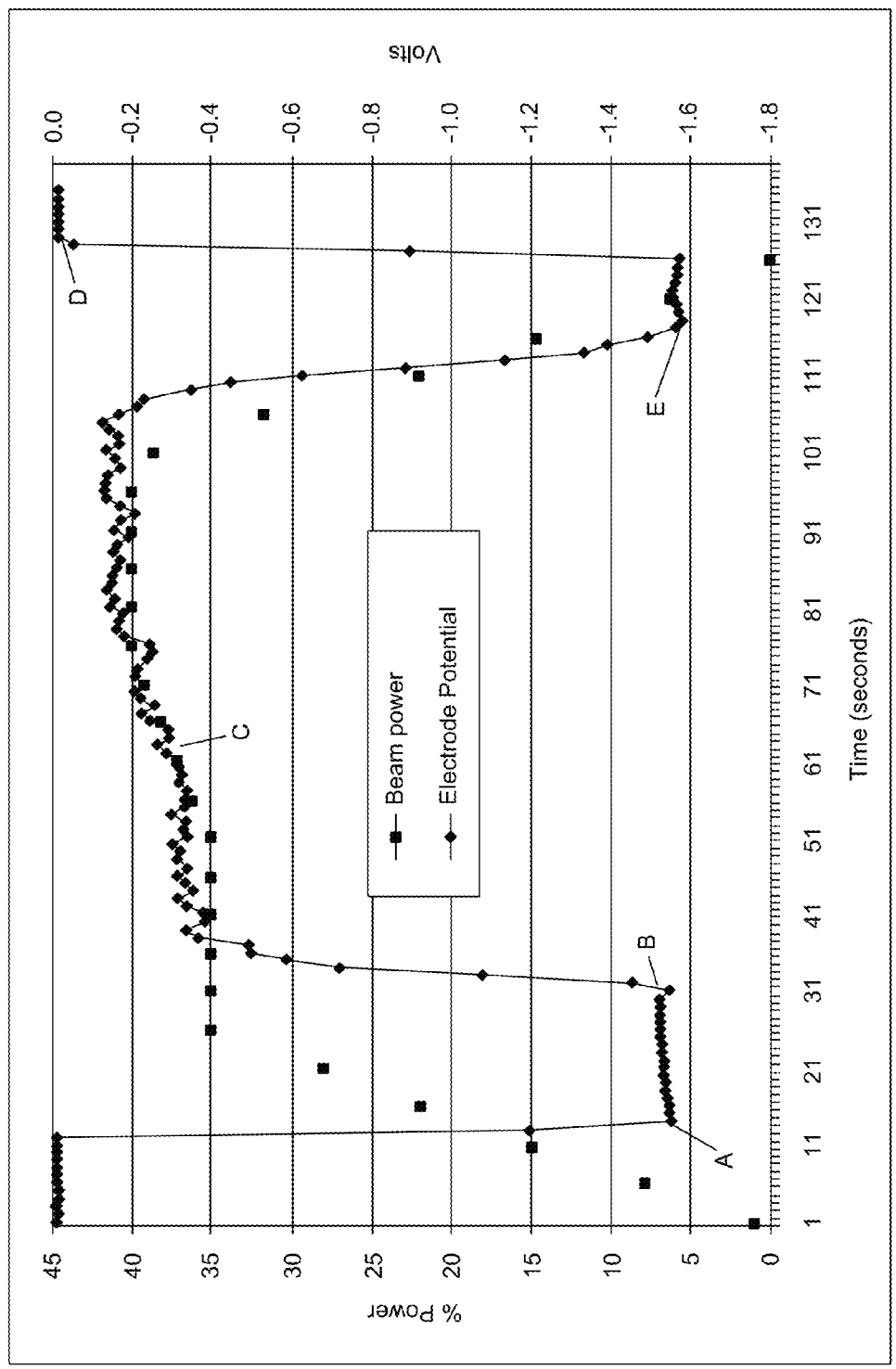
FIG. 12 is a chart of electron-beam power and voltage readings from another test of an electrode according to an embodiment of the present invention mounted in an electron-beam metal evaporation/deposition system.

When the experiment was repeated with a static beam, and a 1 ppm carbon contaminated gold slug, the voltage did not fluctuate, although a similar trend in the data was observed as is shown in FIG. 10. The data obtained in this static beam test are illustrated in FIG. 12. In FIG. 12, points "A," "B," "C," and "D" represent similar points labeled in FIG. 10. FIG. 12 also includes a point "E" where, as the electron-beam power dropped, the gold melt solidified and the voltage from the electrode dropped to approximately −1.6 V. Fluctuation in the observed voltage did not occur because the electron-beam remained focused on a single portion of the gold slug rather than sweeping over "clean" and "dirty" areas of the gold slug.

Figure 11:
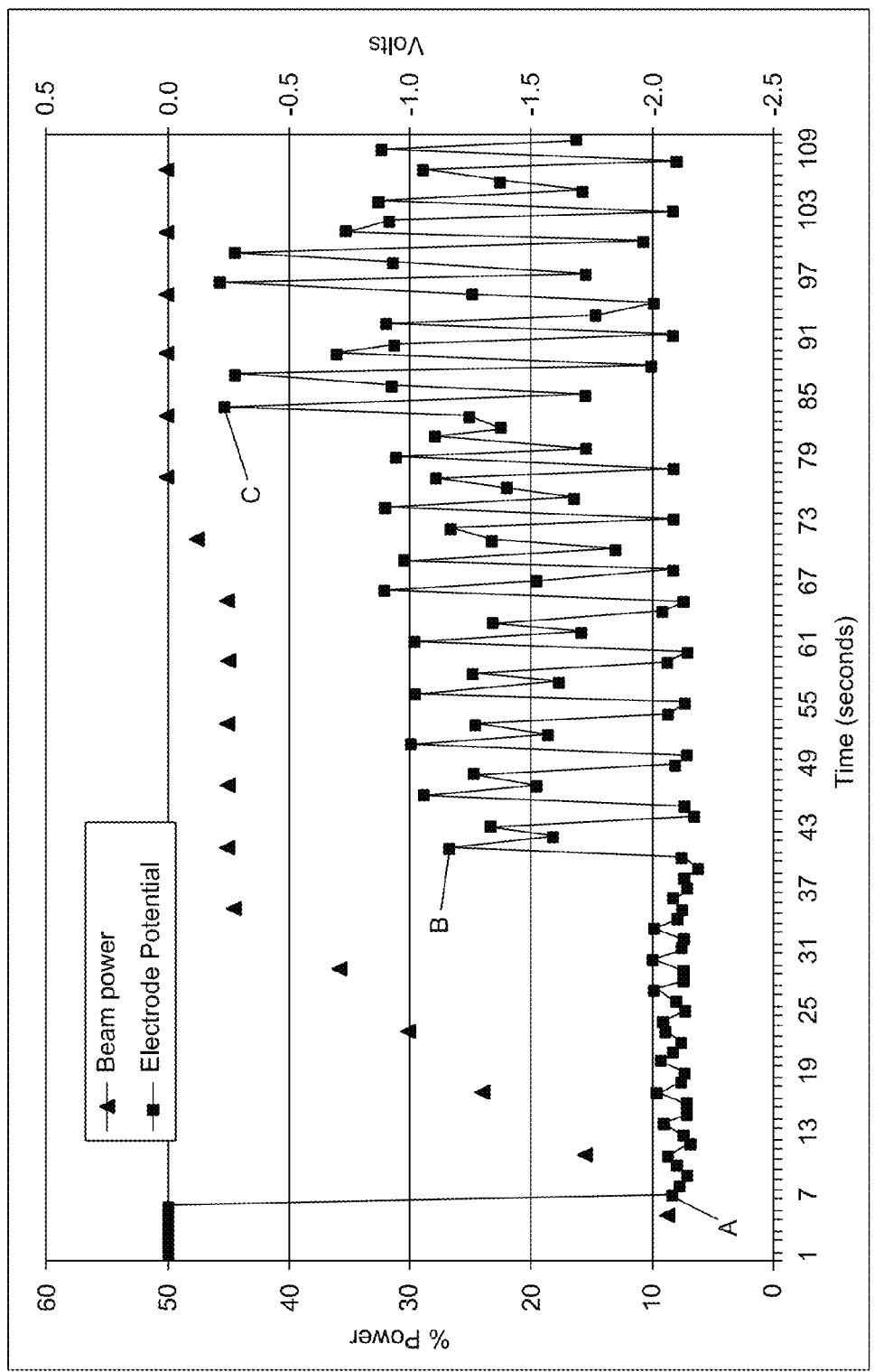
FIG. 11 is a chart of electron-beam power and voltage readings from another test of an electrode according to an embodiment of the present invention mounted in an electron-beam metal evaporation/deposition system.

The experiment described with regard to FIG. 10, utilizing the same recipe with a circular beam sweep pattern of 2 Hz, was repeated using a gold melt with about 30 ppm of carbon on the surface. The data from this repeated experiment is illustrated in FIG. 11. A comparison between FIG. 10 and FIG. 11 illustrates the difference in the voltages observed between the "clean" 1 ppm carbon contaminated slug and the "dirty" 30 ppm carbon contaminated slug. When the beam hit the 30 ppm carbon contaminated slug at point "A," the electrode potential to ground was about two times higher than that observed for the 1 ppm carbon contaminated slug, at −2.2V. It took more power and longer time to melt the 30 ppm carbon contaminated slug than the 1 ppm carbon contaminated slug (note the rightward shift of points "B" and "C" in FIG. 11 from points "B" and "C" in FIG. 10.)

Throughout the ramp and constant power cycle using the 30 ppm carbon contaminated slug, the voltage generated on the electrode followed the same trend as in the experiment using the 1 ppm carbon contaminated slug, although the entire curve shifted towards more negative voltages, indicating that more electrons were collected by the electrode. When the 30 ppm carbon contaminated gold slug turned molten, the voltage dropped, but it stayed at an overall higher negative voltage than observed for the molten slug having the 1 ppm carbon contamination. The range and standard deviation of voltage readings from the molten 30 ppm carbon contaminated gold slug were significantly greater than for the 1 ppm carbon contaminated gold slug, as can be seen by comparing FIG. 10 to FIG. 11.

It was found that a gold slug with more than about 30 ppm of carbon on the surface will not turn completely molten with even 90% beam power of 15 KW. This indicates that this level of carbon contamination is sufficient to reflect or backscatter so many electrons from a surface of a gold slug than not enough electrons can reach the gold slug to impart energy sufficient to completely melt the slug.

Although both the 1 ppm and 30 ppm carbon contaminated gold slugs appeared to be clean and shiny optically, SEM inspection of the 30 ppm carbon contaminated slug revealed specks of carbon particles on the surface. A gold melt made from a low carbon content material (<1 ppm) has no visible carbon particles in SEM inspection. An EDX survey of the 30 ppm carbon contaminated gold slug showed a strong carbon signal indicative carbon contamination on the slug. An EDX survey of the <1 ppm carbon contaminated gold slug showed a carbon peak much attenuated from that in the EDX survey of the 30 ppm carbon contaminated gold slug.

Using the electrode potential as a reference, an observed voltage of −0.4V was determined as the baseline voltage for a good clean gold melt, whereas a voltage of less than −0.8 V was determined to be indicative of a carbon contaminated gold melt.

Based on this data, a voltage of −0.8 volts could be established as the voltage threshold level for the evaporator configuration utilized in this experiment. If a voltage data point peak was observed at less than −0.8 volts, this would be an indication of a potentially contaminated gold slug in the particular evaporator used in this experiment. It should be appreciated that other metals and/or evaporators may have different voltage thresholds. However, applicant has determined that similar differences between clean and contaminated metal slugs will exhibit similar results with regard to a shift in a mean and a standard deviation or range of voltage data points observed on an electrode located in the deposition chamber of an e-beam evaporator as were observed in this experiment.

This experiment also showed that in a metal evaporator, a first gold slug having a relatively low level of carbon contamination will show a drop in voltage on an electrode placed in the deposition chamber of the metal evaporator that is of a lesser magnitude than a drop in voltage for a gold slug having a higher amount of carbon contamination. Further, the fluctuation in voltage readings on the electrode for a metal evaporator operating with a dirtier gold slug will be significantly greater than fluctuations in voltage readings when a cleaner gold slug is used.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A system for detecting impurities in a metal slug from which metal is evaporated during operation of an electron-beam metal evaporation and deposition apparatus, the system comprising:
  an electrode to be positioned within a vacuum chamber of the electron-beam metal evaporation and deposition apparatus and to collect electrons backscattered from the metal slug;
  one or more insulating standoffs to support the electrode in a position in which there is an unobstructed straight line path between a portion of the electrode and a surface of the metal slug and to provide an unobstructed straight line path between a surface of the metal slug and a wafer positioned for processing in the electron-beam metal evaporation and deposition apparatus;
  an electrical meter to receive a first signal from the electrode and output a second signal responsive to the receipt of the first signal; and
  a controller programmed to receive the second signal from the electrical meter and provide an indication of an impurity concentration in the metal slug responsive to a characteristic of the second signal.

2. The system of claim 1 wherein the electrical meter includes at least one of a voltage meter and a current meter.

3. The system of claim 2 wherein the controller is programmed to provide an indication of an undesirable impurity concentration in the metal slug responsive to one of a current measurement and a voltage measurement from the electrode displaying a characteristic which violates a predefined statistical process control rule.

4. The system of claim 1 wherein the one or more insulating standoffs electrically isolate the electrode from interior surfaces of the electron-beam metal evaporation and deposition apparatus and from ground.

5. The system of claim 1 wherein the electrode includes a ring of metal plating.

6. The system of claim 1 wherein the electrode includes one or more rings of wire.

7. The system of claim 1 wherein the electrode includes a metal screen.

8. The system of claim 1 wherein the electrode includes a plurality of plates.

9. The system of claim 1 wherein the controller is programmed to generate one of a baseline mean and a baseline standard deviation of a series of measurements of the characteristic of the second signal.

10. The system of claim 9 wherein the controller is programmed to detect a shift in the characteristic of the second signal from the baseline mean and to issue a warning responsive to the detection of the shift.

11. The system of claim 9 wherein the controller is programmed to detect a change in a standard deviation of a series of measurements of the characteristic of the second signal from the baseline standard deviation and to issue a warning responsive to the detection of the change.

12. The system of claim 1 having the capability of detecting an impurity level of 30 ppm carbon in the metal slug.

13. A system for detecting impurities in a metal slug from which metal is evaporated during operation of an electron-beam metal evaporation and deposition apparatus, the system comprising:
   means for collecting electrons backscattered from the metal slug;
   one or more insulating standoffs that support the means for collecting electrons backscattered from the metal slug in a position in which there is an unobstructed straight line path between a surface of the metal slug and a wafer positioned for processing in a vacuum chamber of the electron-beam metal evaporation and deposition apparatus; and
   a controller programmed to receive a signal from the means for collecting electrons backscattered from the metal slug and to provide an indication of an impurity concentration in the metal slug responsive to a characteristic of the signal.

14. The system of claim 13 wherein the one or more insulating standoffs further support the means for collecting electrons backscattered from the metal slug in a position in which there is an unobstructed straight line path between a portion of the means for collecting electrons backscattered from the metal slug and a surface of the metal slug.

15. The system of claim 13 wherein the one or more insulating standoffs further electrically isolate the means for collecting electrons backscattered from the metal slug from interior surfaces of the electron-beam metal evaporation and deposition apparatus and from ground.

16. A method for increasing the production yield of a semiconductor manufacturing process utilizing an electron-beam metal evaporation and deposition process, the method comprising:
   mounting an electrode within a vacuum chamber of an electron-beam metal evaporation and deposition apparatus in a position in which electrons backscattered from a metal slug during operation of the electron-beam metal evaporation and deposition apparatus will impact the electrode and generate a signal; and
   electrically coupling the electrode to a controller programmed to receive the signal from the electrode and provide an indication of an impurity concentration in the metal slug responsive to a characteristic of the signal.

17. The method of claim 16 wherein mounting the electrode within the vacuum chamber includes mounting the electrode within the vacuum chamber with one or more insulating standoffs that support the electrode in a position in which there is an unobstructed straight line path between a portion of the electrode and a surface of the metal slug and that provide an unobstructed straight line path between a surface of the metal slug and a wafer positioned for processing in the electron-beam metal evaporation and deposition apparatus.

18. The method of claim 17 wherein mounting the electrode within the vacuum chamber includes electrically isolating the electrode from interior surfaces of the electron-beam metal evaporation and deposition apparatus and from ground.

19. The method of claim 16 further comprising programming the controller to issue a warning responsive to the characteristic of the signal violating one or more statistical process control rules.

20. The method of claim 19 further comprising discontinuing operation of the electron-beam metal evaporation and deposition apparatus responsive to the issuance of the warning.

* * * * *